(12) United States Patent
Hazra et al.

(10) Patent No.: US 12,254,670 B2
(45) Date of Patent: Mar. 18, 2025

(54) RADAR-BASED ACTIVITY CLASSIFICATION

(71) Applicant: Infineon Technologies AG, Neubiberg (DE)

(72) Inventors: Souvik Hazra, Munich (DE); Avik Santra, Munich (DE)

(73) Assignee: Infineon Technologies AG, Neubiberg (DE)

( * ) Notice: Subject to any disclaimer, the term of this patent is extended or adjusted under 35 U.S.C. 154(b) by 352 days.

(21) Appl. No.: 17/877,575

(22) Filed: Jul. 29, 2022

(65) Prior Publication Data

US 2024/0037908 A1   Feb. 1, 2024

(51) Int. Cl.
| G06V 10/764 | (2022.01) |
| G01S 13/89 | (2006.01) |
| G06V 10/82 | (2022.01) |
| G06V 10/84 | (2022.01) |
| G06V 40/20 | (2022.01) |

(52) U.S. Cl.
CPC ............ *G06V 10/764* (2022.01); *G01S 13/89* (2013.01); *G06V 10/82* (2022.01); *G06V 10/84* (2022.01); *G06V 40/23* (2022.01)

(58) Field of Classification Search
None
See application file for complete search history.

(56) References Cited

U.S. PATENT DOCUMENTS

| 4,241,347 | A | 12/1980 | Albanese et al. |
| 6,147,572 | A | 11/2000 | Kaminski et al. |
| 6,414,631 | B1 | 7/2002 | Fujimoto |
| 6,636,174 | B2 | 10/2003 | Arikan et al. |
| 7,048,973 | B2 | 5/2006 | Sakamoto et al. |
| 7,057,564 | B2 | 6/2006 | Tsai et al. |
| 7,171,052 | B2 | 1/2007 | Park |

(Continued)

FOREIGN PATENT DOCUMENTS

| CN | 1463161 A | 12/2003 |
| CN | 1716695 A | 1/2006 |

(Continued)

OTHER PUBLICATIONS

Thayaparan, T. et al., "Intelligent target recognition using micro-Doppler radar signatures," Defence R&D Canada, Radar Sensor Technology III, Proc. of SPIE, vol. 7308, 730817, Dec. 9, 2009, 11 pages.

(Continued)

*Primary Examiner* — Darryl V Dottin
(74) *Attorney, Agent, or Firm* — Slater Matsil, LLP

(57) ABSTRACT

In an embodiment, a method includes: receiving raw data from a millimeter-wave radar sensor; generating a first radar-Doppler image based on the raw data; generating a first radar point cloud based on the first radar-Doppler image; using a graph encoder to generate a first graph representation vector indicative of one or more relationships between two or more parts of the target based on the first radar point cloud; generating a first cadence velocity diagram indicative of a periodicity of movement of one or more parts of the target based on the first radar-Doppler image; and classifying an activity of a target based on the first graph representation vector and the first cadence velocity diagram.

20 Claims, 7 Drawing Sheets

(56) References Cited

U.S. PATENT DOCUMENTS

| | | |
|---|---|---|
| 7,317,417 B2 | 1/2008 | Arikan et al. |
| 7,596,241 B2 | 9/2009 | Rittscher et al. |
| 7,692,574 B2 | 4/2010 | Nakagawa |
| 7,873,326 B2 | 1/2011 | Sadr |
| 7,889,147 B2 | 2/2011 | Tam et al. |
| 8,228,382 B2 | 7/2012 | Pattikonda |
| 8,497,805 B2 | 7/2013 | Rofougaran et al. |
| 8,659,369 B2 | 2/2014 | Rofougaran et al. |
| 8,731,502 B2 | 5/2014 | Salle et al. |
| 8,836,596 B2 | 9/2014 | Richards et al. |
| 8,847,814 B2 | 9/2014 | Himmelstoss et al. |
| 8,860,532 B2 | 10/2014 | Gong et al. |
| 8,976,061 B2 | 3/2015 | Chowdhury |
| 9,172,132 B2 | 10/2015 | Kam et al. |
| 9,182,476 B2 | 11/2015 | Wintermantel |
| 9,202,105 B1 | 12/2015 | Wang et al. |
| 9,229,102 B1 | 1/2016 | Wright et al. |
| 9,413,079 B2 | 8/2016 | Kamgaing et al. |
| 9,495,600 B2 | 11/2016 | Heu et al. |
| 9,886,095 B2 | 2/2018 | Pothier |
| 9,935,065 B1 | 4/2018 | Baheti et al. |
| 10,795,012 B2 | 10/2020 | Santra et al. |
| 2003/0179127 A1 | 9/2003 | Wienand |
| 2004/0238857 A1 | 12/2004 | Beroz et al. |
| 2006/0001572 A1 | 1/2006 | Gaucher et al. |
| 2006/0049995 A1 | 3/2006 | Imaoka et al. |
| 2006/0067456 A1 | 3/2006 | Ku et al. |
| 2007/0210959 A1 | 9/2007 | Herd et al. |
| 2008/0106460 A1 | 5/2008 | Kurtz et al. |
| 2008/0238759 A1 | 10/2008 | Carocari et al. |
| 2008/0291115 A1 | 11/2008 | Doan et al. |
| 2008/0308917 A1 | 12/2008 | Pressel et al. |
| 2009/0073026 A1 | 3/2009 | Nakagawa |
| 2009/0085815 A1 | 4/2009 | Jakab et al. |
| 2009/0153428 A1 | 6/2009 | Rofougaran et al. |
| 2009/0315761 A1 | 12/2009 | Walter et al. |
| 2010/0207805 A1 | 8/2010 | Haworth |
| 2011/0299433 A1 | 12/2011 | Darabi et al. |
| 2012/0087230 A1 | 4/2012 | Guo et al. |
| 2012/0092284 A1 | 4/2012 | Rofougaran et al. |
| 2012/0116231 A1 | 5/2012 | Liao et al. |
| 2012/0195161 A1 | 8/2012 | Little et al. |
| 2012/0206339 A1 | 8/2012 | Dahl |
| 2012/0265486 A1 | 10/2012 | Klofer et al. |
| 2012/0268314 A1 | 10/2012 | Kuwahara et al. |
| 2012/0280900 A1 | 11/2012 | Wang et al. |
| 2013/0027240 A1 | 1/2013 | Chowdhury |
| 2013/0106673 A1 | 5/2013 | McCormack et al. |
| 2014/0028542 A1 | 1/2014 | Lovitt et al. |
| 2014/0070994 A1 | 3/2014 | Schmalenberg et al. |
| 2014/0145883 A1 | 5/2014 | Baks et al. |
| 2014/0324888 A1 | 10/2014 | Xie et al. |
| 2015/0181840 A1 | 7/2015 | Tupin, Jr. et al. |
| 2015/0185316 A1 | 7/2015 | Rao et al. |
| 2015/0212198 A1 | 7/2015 | Nishio et al. |
| 2015/0243575 A1 | 8/2015 | Strothmann et al. |
| 2015/0277569 A1 | 10/2015 | Sprenger et al. |
| 2015/0325925 A1 | 11/2015 | Kamgaing et al. |
| 2015/0346820 A1 | 12/2015 | Poupyrev et al. |
| 2015/0348821 A1 | 12/2015 | Iwanaga et al. |
| 2015/0364816 A1 | 12/2015 | Murugan et al. |
| 2016/0018511 A1 | 1/2016 | Nayyar et al. |
| 2016/0041617 A1 | 2/2016 | Poupyrev |
| 2016/0041618 A1 | 2/2016 | Poupyrev |
| 2016/0061942 A1 | 3/2016 | Rao et al. |
| 2016/0061947 A1 | 3/2016 | Patole et al. |
| 2016/0098089 A1 | 4/2016 | Poupyrev |
| 2016/0103213 A1 | 4/2016 | Ikram et al. |
| 2016/0109566 A1 | 4/2016 | Liu et al. |
| 2016/0118353 A1 | 4/2016 | Ahrens et al. |
| 2016/0135655 A1 | 5/2016 | Ahn et al. |
| 2016/0146931 A1 | 5/2016 | Rao et al. |
| 2016/0146933 A1 | 5/2016 | Rao et al. |
| 2016/0178730 A1 | 6/2016 | Trotta et al. |
| 2016/0187462 A1 | 6/2016 | Altus et al. |
| 2016/0191232 A1 | 6/2016 | Subburaj et al. |
| 2016/0223651 A1 | 8/2016 | Kamo et al. |
| 2016/0240907 A1 | 8/2016 | Haroun |
| 2016/0249133 A1 | 8/2016 | Sorensen |
| 2016/0252607 A1 | 9/2016 | Saboo et al. |
| 2016/0259037 A1 | 9/2016 | Molchanov et al. |
| 2016/0266233 A1 | 9/2016 | Mansour |
| 2016/0269815 A1 | 9/2016 | Liao et al. |
| 2016/0291130 A1 | 10/2016 | Ginsburg et al. |
| 2016/0299215 A1 | 10/2016 | Dandu et al. |
| 2016/0306034 A1 | 10/2016 | Trotta et al. |
| 2016/0320852 A1 | 11/2016 | Poupyrev |
| 2016/0320853 A1 | 11/2016 | Lien et al. |
| 2016/0327633 A1 | 11/2016 | Kumar Y.B. et al. |
| 2016/0334502 A1 | 11/2016 | Ali et al. |
| 2016/0349845 A1 | 12/2016 | Poupyrev et al. |
| 2017/0033062 A1 | 2/2017 | Liu et al. |
| 2017/0045607 A1 | 2/2017 | Bharadwaj et al. |
| 2017/0052618 A1 | 2/2017 | Lee et al. |
| 2017/0054449 A1 | 2/2017 | Mani et al. |
| 2017/0060254 A1 | 3/2017 | Molchanov et al. |
| 2017/0070952 A1 | 3/2017 | Balakrishnan et al. |
| 2017/0074974 A1 | 3/2017 | Rao et al. |
| 2017/0074980 A1 | 3/2017 | Adib et al. |
| 2017/0090014 A1 | 3/2017 | Subburaj et al. |
| 2017/0090015 A1 | 3/2017 | Breen et al. |
| 2017/0115377 A1 | 4/2017 | Giannini et al. |
| 2017/0131395 A1 | 5/2017 | Reynolds et al. |
| 2017/0139036 A1 | 5/2017 | Nayyar et al. |
| 2017/0141453 A1 | 5/2017 | Waelde et al. |
| 2017/0170947 A1 | 6/2017 | Yang |
| 2017/0176574 A1 | 6/2017 | Eswaran et al. |
| 2017/0192847 A1 | 7/2017 | Rao et al. |
| 2017/0201019 A1 | 7/2017 | Trotta |
| 2017/0212597 A1 | 7/2017 | Mishra |
| 2017/0364160 A1 | 12/2017 | Malysa et al. |
| 2018/0046255 A1 | 2/2018 | Rothera et al. |
| 2018/0071473 A1 | 3/2018 | Trotta et al. |
| 2018/0101239 A1 | 4/2018 | Yin et al. |
| 2021/0117659 A1 | 4/2021 | Foroozan et al. |
| 2021/0141092 A1* | 5/2021 | Chen ............... G01S 13/867 |
| 2021/0156960 A1* | 5/2021 | Popov ............... G01S 13/89 |
| 2021/0396843 A1 | 12/2021 | Santra et al. |

FOREIGN PATENT DOCUMENTS

| | | |
|---|---|---|
| CN | 101490578 A | 7/2009 |
| CN | 101585361 A | 11/2009 |
| CN | 102788969 A | 11/2012 |
| CN | 102967854 A | 3/2013 |
| CN | 103529444 A | 1/2014 |
| CN | 203950036 U | 11/2014 |
| DE | 102008054570 A1 | 6/2010 |
| DE | 102011100907 A1 | 1/2012 |
| DE | 102011075725 A1 | 11/2012 |
| DE | 102014118063 A1 | 7/2015 |
| GB | 2247799 A | 3/1992 |
| JP | 2001174539 A | 6/2001 |
| JP | 2004198312 A | 7/2004 |
| JP | 2006234513 A | 9/2006 |
| JP | 2008029025 A | 2/2008 |
| JP | 2008089614 A | 4/2008 |
| JP | 2009069124 A | 4/2009 |
| JP | 2011529181 A | 12/2011 |
| JP | 2012112861 A | 6/2012 |
| JP | 2013521508 A | 6/2013 |
| JP | 2014055957 A | 3/2014 |
| KR | 20090063166 A | 6/2009 |
| KR | 20140082815 A | 7/2014 |
| WO | 2007060069 A1 | 5/2007 |
| WO | 2013009473 A2 | 1/2013 |
| WO | 2016033361 A1 | 3/2016 |

OTHER PUBLICATIONS

Tu, Jianxuan et al., "Fast Acquisition of Heart Rate in Noncontact Vital Sign Radar Measurement Using Time-Window-Variation Tech

(56) References Cited

OTHER PUBLICATIONS nique", IEEE Transactions on Instrumentation and Measurement, vol. 65, No. 1, Jan. 2016, pp. 112-122.
Vinci, Gabor et al., "Microwave Interferometer Radar-Based Vital Sign Detection for Driver Monitoring Systems", IEEE MTT-S International Conference on Microwaves for Intelligent Mobility, Apr. 27-29, 2015, 4 pages.
Vinci, Gabor et al., "Six-Port Radar Sensor for Remote Respiration Rate and Heartbeat Vital-Sign Monitoring", IEEE Transactions on Microwave Theory and Techniques, vol. 61, No. 5, May 2013, pp. 2093-2100.
Wang, Fu-Kang et al., "Wrist Pulse Rate Monitor Using Self-Injection-Locked Radar Technology", Biosensors, MDPI, Oct. 26, 2016, 12 pages.
Wang, Y. et al., "Dynamic Graph CNN for Learning on Point Clouds," arXiv:1801.07829v2, ACM Trans. Graph., vol. 1, No. 1, Article 1, Jan. 2019, 13 pages.
Wilder, Carol N., et al., "Respiratory patterns in infant cry," Canada Journal of Speech, Human Communication Winter, 1974-75, http://cjslpa.ca/files/1974_HumComm_Vol_01/No_03_2-60/Wilder_Baken_HumComm_1974.pdf, winter of 1974, pp. 18-34.
Will, Christoph et al., "Advanced Template Matching Algorithm for Instantaneous Heartbeat Detection using Continuous Wave Radar Systems", ResearchGate, May 2017, 5 pages.
Will, Christoph et al., "Human Target Detection, Tracking, and Classification Using 24-GHz FMCW Radar", IEEE Sensors Journal, vol. 19, No. 17, Sep. 1, 2019, pp. 7283-7299.
Will, Christoph et al., "Local Pulse Wave Detection using Continuous Wave Radar Systems", IEEE Journal of Electromagnetics, RF and Microwaves in Medicine and Biology, Oct. 25, 2017, 9 pages.
Will, Christoph et al., "Radar-Based Heart Sound Detection", Scientific Reports, www.nature.com/scientificreports, Jul. 26, 2018, 15 pages.
Xin, Qin et al., "Signal Processing for Digital Beamforming FMCW SAR," Hindawi Publishing Corporation, Mathematical Problems in Engineering, vol. 2014, Article ID 859890, http://dx.doi.org/10.1155/2014/859890, Apr. 15, 2014, 11 pages.
"BT24MTR11 Using BGT24MTR11 in Low Power Applications 24 GHz Rader," Application Note AN341, Revision: Rev 1.0, Infineon Technologies AG, Munich, Germany, Dec. 2, 2013, 25 pages.
Björklund, S. et al., "Features for micro-Doppler based activity classification," Linköping University Post Print, Jul. 24, 2015, 14 pages.
Chen, Xiaolong et al., "Detection and Extraction of Marine Target with Micromotion via Short-Time Fractional Fourier Transform in Sparse Domain," IEEE International Conference on Signal Processing, Communications and Computing, ICSPCC, Aug. 5-8, 2016, 5 pages.
Chen, Xiaolong et al., "Detection and Extraction of Target with Micromotion in Spiky Sea Clutter via Short-Time Fractional Fourier Transform", IEEE Transactions on Geoscience and Remote Sensing, vol. 52, No. 2, Feb. 2014, pp. 1002-1018.
Chioukh, Lydia et al., "Noise and Sensitivity of Harmonic Radar Architecture for Remote Sensing and Detection of Vital Signs", IEEE Transactions on Microwave Theory and Techniques, vol. 62, No. 9, Sep. 2014, pp. 1847-1855.
Chuanhua, Du, "FMCW Radar Range-Doppler Processing and Beam Formation Technology," Chinese Doctoral Dissertations & Master's Theses Full Text Database (Masters)—Information Science and Technology Series, China National Knowledge Infrastructure, ISSN 1674-0246, CN 11-9144/G, Dec. 16, 2004-Mar. 2015, 14 pages.
Clemente, C. et al., "A Novel Algorithm for Radar Classification Based on Doppler Characteristics Exploiting Orthogonal Pseudo-Zernike Polynomials," IEEE Transactions on Aerospace and Electronic Systems, vol. 51, No. 1, Jan. 2015, 14 pages.
Deacon, Peter et al., "Frequency Modulated Continuous Wave (FMCW) Radar," Design Team 6 Technical Lecture, Nov. 9, 2011, 27 pages.

Dham, Vivek "Programming Chirp Parameters in TI Radar Devices," Application Report SWRA553, Texas Instruments, May 2017, 15 pages.
Diederichs, Kailtyn et al., "Wireless Biometric Individual Identification Utilizing Millimeter Waves", IEEE Sensors etters, vol. 1, No. 1, IEEE Sensors Council 3500104, Feb. 2017, 4 pages.
Futia, G., "Graph Representation Learning—The Encoder-Decoder Model (Part 2)," GraphEDM-Series, Towards Data Science, May 26, 2021, 8 pages.
Gigie, Andrew et al., "Novel Approach for Vibration Detection Using Indented Radar", Progess in Electromagnetic Research C, vol. 87, pp. 147-162, Oct. 4, 2018.
Gouveia, Carolina et al., "A Review on Methods for Random Motion Detection and Compensation in Bio-Radar Systems", Sensors, MDPI, Jan. 31, 2019, 17 pages.
Gu, Changzhan et al., "Assessment of Human Respiration Patterns via Noncontact Sensing Using Doppler Multi-Radar System", Sensors Mar. 2015, 15(3), 6383-6398, doi: 10.3390/s150306383, 17 pages.
Gu, Changzhan et al., "Deep Neural Network based Body Movement Cancellation for Doppler Radar Vital Sign Detection", IEEE MTT-S International Wireless Symposium (IWS) May 19-22, 2019, 3 pages.
Gu, Changzhu "Short-Range Noncontact Sensors for Healthcare and Other Emerginng Applications: A Review", Sensors, MDPI, Jul. 26, 2016, 24 pages.
Gu, Changzhan et al., "From Tumor Targeting to Speed Monitoring", IEEE Microwave Magazine, ResearchGate, Jun. 2014, 11 pages.
Guercan, Yalin "Super-resolution Algorithms for Joint Range-Azimuth-Doppler Estimation in Automotive Radars," Technische Universitet Delft, TUDelft University of Technology Challenge the Future, Jan. 25, 2017, 72 pages.
Hazra, S. et al., "Cross-modal Learning of Graph Representations using Radar Point Cloud for Long-Range Gesture Recognition," arXiv:2203.17066v2, May 19, 2022, 5 pages.
Hu, Wei et al., "Noncontact Accurate Measurement of Cardiopulmonary Activity Using a Compact Quadrature Doppler Radar Sensor", IEEE Transactions on Biomedical Engineering, vol. 61, No. 3, Mar. 2014, pp. 725-735.
Immoreev, I. Ya. "Ultrawideband Radars: Features and Capabilities", Journal of Communications Technology and Electronics, ISSN: 1064-2269, vol. 54, No. 1, Feb. 8, 2009, pp. 1-26.
Inac, Ozgur et al., "A Phased Array RFIC with Built-In Self-Test Capabilities," IEEE Transactions on Microwave Theory and Techniques, vol. 60, No. 1, Jan. 2012, 10 pages.
Jin, F., "Millimeter-wave Radar Point Cloud Classification and Interference Mitigation," The University of Arizona, University Libraries, UA Campus Repository, downloaded Jun. 23, 2022, 109 pages.
Killedar, Abdulraheem "XWR1xxx Power Management Optimizations—Low Cost LC Filter Solution," Application Report SWRA577, Texas Instruments, Oct. 2017, 19 pages.
Kishore, N. et al., "Millimeter Wave Antenna for Intelligent Transportation Systems Application", Journal of Microwaves, Optoelectronics and Electromagnetic Applications, vol. 17, No. 1, Mar. 2018, pp. 171-178.
Kizhakkel, V., "Pulsed Radar Target Recognition Based on Micro-Doppler Signatures Using Wavelet Analysis", A Thesis, Graduate Program in Electrical and Computer Engineering, Ohio State University, Jan. 2013-May 2013, 118 pages.
Kuehnke, Lutz, "Phased Array Calibration Procedures Based on Measured Element Patterns," 2001 Eleventh International Conference on Antennas and Propagation, IEEE Conf., Publ. No. 480, Apr. 17-20, 2001, 4 pages.
Li, Changzhi et al., "A Review on Recent Advances in Doppler Radar Sensors for Noncontact Healthcare Monitoring", IEEE Transactions on Microwave Theory and Techniques, vol. 61, No. 5, May 2013, pp. 2046-2060.
Li, Changzhi et al., "A Review on Recent Progress of Portable Short-Range Noncontact Microwave Radar Systems", IEEE Transactions on Microwave Theory and Techniques, vol. 65, No. 5, May 2017, pp. 1692-1706.

(56) References Cited

OTHER PUBLICATIONS

Li, Changzhi et al., "Random Body Movement Cancellation in Doppler Radar Vital Sign Detection", IEEE Transactions on Microwave Theory and Techniques, vol. 56, No. 12, Dec. 2008, pp. 3143-3152.

Li, Changzhi et al., "Robust Overnight Monitoring of Human Vital Signs by a Non-contact Respiration and Heartbeat Detector", IEEE Proceedings of the 28th EMBS Annual International Conference, FrA05.5, Aug. 30-Sep. 3, 2006, 4 pages.

Li, Changzhi "Vital-sign monitoring on the go", Sensors news and views, www.nature.com/naturelectronics, Nature Electronics, vol. 2, Jun. 2019, 2 pages.

Lim, Soo-Chul et al., "Expansion of Smartwatch Touch Interface from Touchscreen to Around Device Interface Using Infrared Line Image Sensors," Sensors 2015, ISSN 1424-8220, vol. 15, 16642-16653, doi:10.3390/s150716642, www.mdpi.com/journal/sensors, Jul. 15, 2009, 12 pages.

Lin, Jau-Jr et al., "Design of an FMCW radar baseband signal processing system for automotive application," SpringerPlus a SpringerOpen Journal, (2016) 5:42, http://creativecommons.org/licenses/by/4.0/, DOI 10.1186/s40064-015-1583-5; Jan. 2016, 16 pages.

Massagram, Wansuree et al., "Assessment of Heart Rate Variability and Respiratory Sinus Arrhythmia via Doppler Radar", IEEE Transactions on Microwave Theory and Techniques, vol. 57, No. 10, Oct. 2009, pp. 2542-2549.

Mercuri, Marco et al., "Vital-sign monitoring and spatial tracking of multiple people using a contactless radar-based sensor", Nature Electronics, vol. 2, Articles, https://doi.org/10.1038/s41928-019-0258-6, Jun. 2019, 13 pages.

Meta AI, "Detectron2: A PyTorch-based modular object detection library," ML Applications, Open Sourse, Oct. 10, 2019, 8 pages.

Microwave Journal Frequency Matters, "Single-Chip 24 GHz Radar Front End," Infineon Technologies AG, www.microwavejournal.com/articles/print/21553-single-chip-24-ghz-radar-front-end, Feb. 13, 2014, 2 pages.

Mostov, K., et al., "Medical applications of shortwave FM radar: Remote monitoring of cardiac and respiratory motion", Am. Assoc. Phys. Med., 37(3), Mar. 2010, pp. 1332-1338.

Oguntala, G et al., "Indoor location identification technologies for real-time IoT-based applications: an inclusive survey", Elsevier Inc., http://hdl.handle.net/10454/16634, Oct. 2018, 21 pages.

Peng, Zhengyu et al., "A Portable FMCW Interferometry Radar with Programmable Low-IF Architecture for Localization, ISAR Imaging, and Vial Sign Tracking", IEEE Transactions on Microwave Theory and Techniques, Dec. 15, 2016, 11 pages.

Qadir, Shahida G., et al., "Focused ISAR Imaging of Rotating Target in Far-Field Compact Range Anechoic Chamber," 14th International Conference on Aerospace Sciences & Aviation Technology, ASAT-14-241-IP, May 24-26, 2011, 7 pages.

Richards, Mark A., "Fundamentals of Radar Signal Processing," McGraw Hill Electronic Engineering, ISBN: 0-07-144474-2, Jun. 2005, 93 pages.

Sakamoto, Takuya et al., "Feature-Based Correlation and Topological Similarity for Interbeat Interval Estimation Using Ultrawideband Radar", IEEE Transactions on Biomedical Engineering, vol. 63, No. 4, Apr. 2016, pp. 747-757.

Santra, Avik et al., "Short-range multi-mode continuous-wave radar for vital sign measurement and imaging", ResearchGate, Conference Paper, Apr. 2018, 6 pages.

Schroff, Florian et al., "FaceNet: A Unified Embedding for Face Recognition and Clustering," CVF, CVPR2015, IEEE Computer Society Conference on Computer Vision and Pattern Recognition; Mar. 12, 2015, pp. 815-823.

Simon, W., et al., "Highly Integrated KA-Band Tx Frontend Module Including 8x8 Antenna Array," IMST GmbH, Germany, Asia Pacific Microwave Conference, Dec. 7-10, 2009, 63 pages.

Singh, Aditya et al., "Data-Based Quadrature Imbalance Compensation for a CW Doppler Radar System", https://www.researchgate.net/publication/258793573, IEEE Transactions on Microwave Theory and Techniques, Apr. 2013, 7 pages.

Suleymanov, Suleyman, "Design and Implementation of an FMCW Radar Signal Processing Module for Automotive Applications," Master Thesis, University of Twente, Aug. 31, 2016, 64 pages.

Thayaparan, T. et al., "Micro-Doppler Radar Signatures for Intelligent Target Recognition," Defence Research and Development Canada, Technical Memorandum, DRDC Ottawa TM 2004-170, Sep. 2004, 73 pages.

* cited by examiner

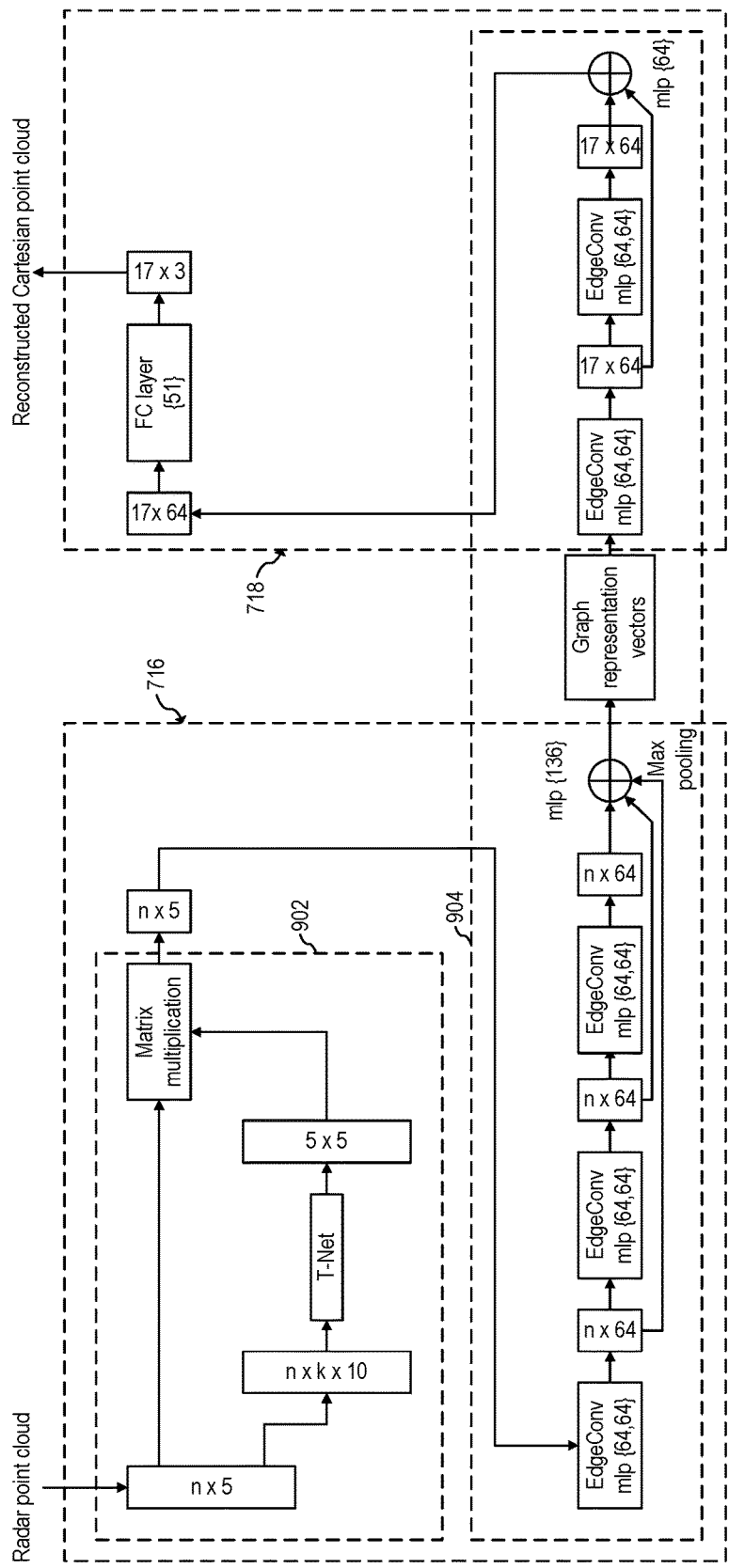
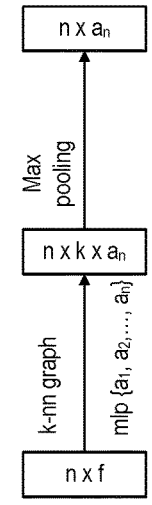
FIG. 9A
FIG. 9B

RADAR-BASED ACTIVITY CLASSIFICATION

TECHNICAL FIELD

The present disclosure relates generally to an electronic system and method, and, in particular embodiments, to radar-based activity classification.

BACKGROUND

Globally, the elderly group (e.g., 65+ years old) is a fast-growing group. Elderly falls account for a significant number of injuries, and many of the injuries are expensive to treat. As a result, elderly fall detection is an active research area.

It may be desirable for a system to automatically detect a fall of a (e.g., elderly) person (e.g., immediately) after the fall occurs, and trigger an alert so that the person is treated soon after the fall. Such a system may advantageously allow for continuous monitoring of a person, and may allow for prompt detection of a fall. People that may benefit from such a system includes people with dementia and other cognitive and/or physical impairments.

Elderly fall detection may be performed in various ways. As a field of growing research, many proposals with different sensors have been developed. Popular systems for elderly fall detection include vision systems and wearable systems.

Vision systems may be used to adequately detect elderly fall detection. However, Vision systems may be expensive, may exhibit low performance in occluded or partially occluded scenarios and low illumination scenarios, and may suffer from privacy concerns.

Wearable systems may also be used for to adequately detect elderly fall detection. However, wearable systems may be uncomfortable to wear and may restrict the freedom of the person wearing it.

SUMMARY

In accordance with an embodiment, a method includes: receiving raw data from a millimeter-wave radar sensor; generating a first radar-Doppler image based on the raw data; generating a first radar point cloud based on the first radar-Doppler image; using a graph encoder to generate a first graph representation vector indicative of one or more relationships between two or more parts of the target based on the first radar point cloud; generating a first cadence velocity diagram indicative of a periodicity of movement of one or more parts of the target based on the first radar-Doppler image; and classifying an activity of a target based on the first graph representation vector and the first cadence velocity diagram.

In accordance with an embodiment, a radar system includes: a radar sensor configured to transmit a plurality of radar signals towards a scene, receive a plurality of reflected radar signals from the scene, and generate raw data based on the plurality of reflected radar signals; and a processing system configured to: generate a first radar image based on the raw data, generate a first radar point cloud based on the first radar image, use a graph encoder to generate a first graph representation vector indicative of one or more relationships between two or more parts of the target based on the first radar point cloud, generate a first cadence velocity diagram indicative of a periodicity of movement of one or more parts of the target based on the first radar image, and classify an activity of a target located in the scene based on the first graph representation vector and the first cadence velocity diagram.

In accordance with an embodiment, a radar system includes: a millimeter-wave radar sensor configured to transmit a plurality of radar signals towards a scene, receive a plurality of reflected radar signals from the scene, and generate raw data based on the plurality of reflected radar signals; and a processing system configured to: generate a plurality of radar-Doppler images based on the raw data, generate a plurality of radar point clouds based on the plurality of radar-Doppler images, use a graph encoder to generate a plurality of graph representation vectors indicative of one or more relationships between two or more parts of the target based on the plurality of radar point clouds, generate a first cadence velocity diagram indicative of a periodicity of movement of one or more parts of the target based on the plurality of radar-Doppler images, and classify an activity of a target located in the scene based on the plurality of graph representation vectors and the first cadence velocity diagram.

BRIEF DESCRIPTION OF THE DRAWINGS

For a more complete understanding of the present invention, and the advantages thereof, reference is now made to the following descriptions taken in conjunction with the accompanying drawings, in which:

FIGS. 9A and 9B illustrate a possible implementation of the graph CNN encoder and decoder of FIG. 7, according to an embodiment of the present invention.

Corresponding numerals and symbols in different figures generally refer to corresponding parts unless otherwise

DETAILED DESCRIPTION OF ILLUSTRATIVE EMBODIMENTS

Figure 1:
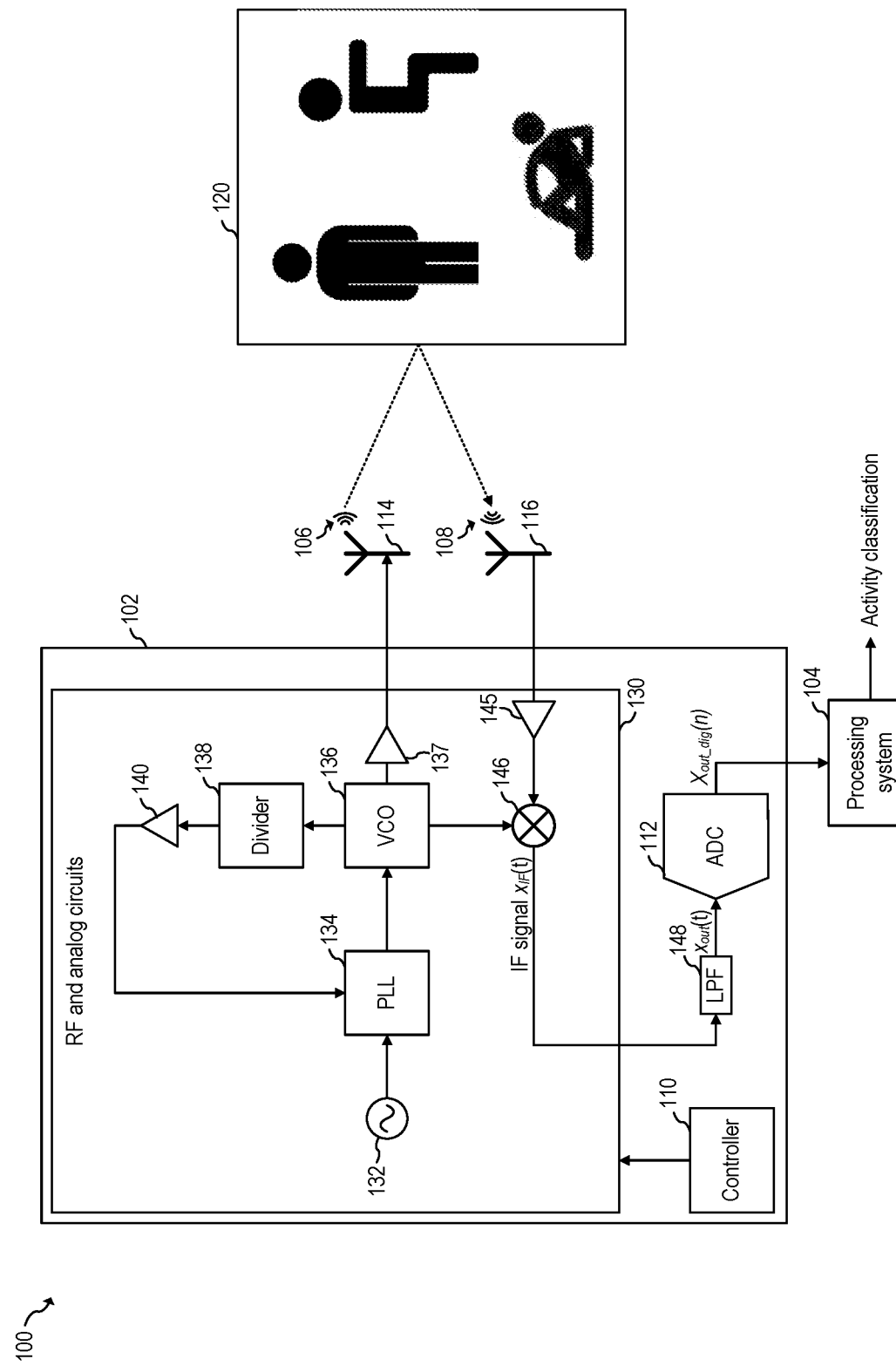
FIG. 1 shows a schematic diagram of a millimeter-wave radar system, according to an embodiment of the present invention.

The making and using of the embodiments disclosed are discussed in detail below. It should be appreciated, however, that the present invention provides many applicable inventive concepts that can be embodied in a wide variety of specific contexts. The specific embodiments discussed are merely illustrative of specific ways to make and use the invention, and do not limit the scope of the invention.

The description below illustrates the various specific details to provide an in-depth understanding of several example embodiments according to the description. The embodiments may be obtained without one or more of the specific details, or with other methods, components, materials and the like. In other cases, known structures, materials or operations are not shown or described in detail so as not to obscure the different aspects of the embodiments. References to "an embodiment" in this description indicate that a particular configuration, structure or feature described in relation to the embodiment is included in at least one embodiment. Consequently, phrases such as "in one embodiment" that may appear at different points of the present description do not necessarily refer exactly to the same embodiment. Furthermore, specific formations, structures or features may be combined in any appropriate manner in one or more embodiments.

Embodiments of the present invention will be described in specific contexts, e.g., a radar-based activity classification system and method, e.g., for elderly fall detection. Embodiments of the present invention may be used for other types of activity classification, such as classifying various human activities (sitting, standing, walking, running, bending over, stretching, etc.), gesture recognition, etc.

Radar-based systems for elderly fall detection have many advantages. Advantages of radar-based systems for elderly fall detection may include: lower cost than vision systems, little or no privacy concerns, less susceptible to a decrease in performance in occluded or partially occluded scenarios and low illumination scenarios, and allowing freedom of movement to the user.

It may be challenging for a radar-based system to distinguish between some activities and a fall. For example, a person sitting down or bent over to pick up something may be mistakenly detected as a fall, thereby causing false positives.

In an embodiment of the present invention, a millimeter-wave radar system is advantageously able to distinguish between similar activities of a target (e.g., a person sitting down versus falling) and, thus, reduce the number of false positives, by encoding a radar point cloud using a graph encoder to obtain graph representation vectors indicative of relationships between different body parts during an activity of the target. In parallel, a cadence-velocity diagram (CVD) is used to extract information about the periodicity of movement of different body parts during the activity of the target. Information from the CVD and the graph representation vectors is used to classify the activity of the target (e.g., a person falling or not falling).

FIG. 1 shows a schematic diagram of millimeter-wave radar system 100, according to an embodiment of the present invention. Millimeter-wave radar system wo includes millimeter-wave radar sensor 102 and processing system 104.

During normal operation, millimeter-wave radar sensor 102 operates as a frequency-modulated continuous-wave (FMCW) radar sensor and transmits a plurality of TX radar signals 106, such as chirps, towards scene 120 using one or more transmitter (TX) antenna 114. The radar signals 106 are generated using RF and analog circuits 130. The radar signals 106 may be, e.g., in the 20 GHz to 122 GHz range. Other frequencies may also be used.

The objects in scene 120 may include one or more static or moving objects, such as tables, walls, chairs, etc., idle and moving humans and animals, as well as periodically-moving objects, such as rotating fans. Other objects may also be present in scene 120.

The radar signals 106 are reflected by objects in scene 120. The reflected radar signals 108, which are also referred to as the echo signal, are received by a plurality of receiving (RX) antennas 116. RF and analog circuits 130 processes the received reflected radar signals 108 using, e.g., band-pass filters (BPFs), low-pass filters (LPFs), mixers, low-noise amplifier (LNA), and/or intermediate frequency (IF) amplifiers in ways known in the art to generate an analog signal $x_{out}(t)$ per receiving antenna 116.

The analog signals $x_{out}(t)$ are converted to raw digital data $x_{out\_dig}(n)$ using analog-to-digital converter (ADC) 112. In some embodiments, the raw digital data $x_{out\_dig}(n)$ is processed by processing system 104 to detect one or more targets and their position, track such targets, and classify the activity of such targets.

Controller 110 controls one or more circuits of millimeter-wave radar sensor 102, such as RF and analog circuit 130 and/or ADC 112. Controller 110 may be implemented, e.g., as a custom digital or mixed signal circuit, for example. Controller 110 may also be implemented in other ways, such as using a general-purpose processor or controller, for example. In some embodiments, processing system 104 implements a portion or all of controller 110.

Processing system 104 may be implemented with a general-purpose processor, controller or digital signal processor (DSP) that includes, for example, combinatorial circuits coupled to a memory. In some embodiments, processing system 104 may be implemented as an application specific integrated circuit (ASIC). In some embodiments, processing system 104 may be implemented with an ARM, RISC, or x86 architecture, for example. In some embodiments, processing system 104 may include an artificial intelligence (AI) accelerator. Some embodiments may use a combination of hardware accelerator and software running on a DSP or general-purpose microcontroller. Other implementations are also possible.

In some embodiments, millimeter-wave radar sensor 102 and a portion or all of processing system 104 may be implemented inside the same integrated circuit (IC). For example, in some embodiments, millimeter-wave radar sensor 102 and a portion or all of processing system 104 may be implemented in respective semiconductor substrates that are integrated in the same package. In other embodiments, millimeter-wave radar sensor 102 and a portion or all of processing system 104 may be implemented in the same monolithic semiconductor substrate. In some embodiments, millimeter-wave radar sensor 102 and processing system 104 are implemented in respective integrated circuits. In some embodiments, a plurality of integrated circuits is used to implement millimeter-wave radar sensor 102. In some embodiments, a plurality of integrated circuits is used to implement processing system 104. Other implementations are also possible.

As a non-limiting example, RF and analog circuits 130 may be implemented, e.g., as shown in FIG. 1. During normal operation, voltage-controlled oscillator (VCO) 136 generates radar signals, such as a linear frequency chirps (e.g., from 57 GHz to 64 GHz, or from 76 GHz to 77 GHz), which are transmitted by transmitting antenna 114. The VCO 136 is controlled by PLL 134, which receives a reference clock signal (e.g., 80 MHz) from reference oscillator 132. PLL 134 is controlled by a loop that includes frequency divider 138 and amplifier 140. Amplifier 137 may be used to drive transmitting antenna 114.

The TX radar signals 106 transmitted by transmitting antenna 114 are reflected by objects in scene 120 and received by receiving antennas 116. The echo received by receiving antennas 116 are mixed with a replica of the signal transmitted by transmitting antenna 114 using respective mixers 146 to produce respective intermediate frequency (IF) signals $x_{IF}(t)$ (also known as beat signals). In some embodiments, the beat signals $x_{IF}(t)$ have a bandwidth between 10 kHz and 1 MHz. Beat signals with a bandwidth lower than 10 kHz or higher than 1 MHz is also possible. Respective amplifiers 145 may be used to receive the reflected radar signals from antennas 116.

Beat signals $x_{IF}(t)$ may be respectively filtered with respective low-pass filters (LPFs) 148 and then sampled by ADC 112. ADC 112 is advantageously capable of sampling the filtered beat signals $x_{out}(t)$ with a sampling frequency that is much smaller than the frequency of the signal received by receiving antennas 116. Using FMCW radars, therefore, advantageously allows for a compact and low-cost implementation of ADC 112, in some embodiments.

The raw digital data $x_{out\_dig}(n)$, which in some embodiments include the digitized version of the filtered beat signals $x_{out}(t)$, is (e.g., temporarily) stored, e.g., in matrices of $N_c \times N_s$ per receiving antenna 116, where $N_c$ is the number of chirps considered in a frame and $N_s$ is the number of transmit samples per chirp, for further processing by processing system 104.

In some embodiments, ADC 112 is a 12-bit ADC with multiple inputs. ADCs with higher resolution, such as 14-bits or higher, or with lower resolution, such as 10-bits, or lower, may also be used. In some embodiments, an ADC per receiver antenna may be used. Other implementations are also possible.

Figure 2:
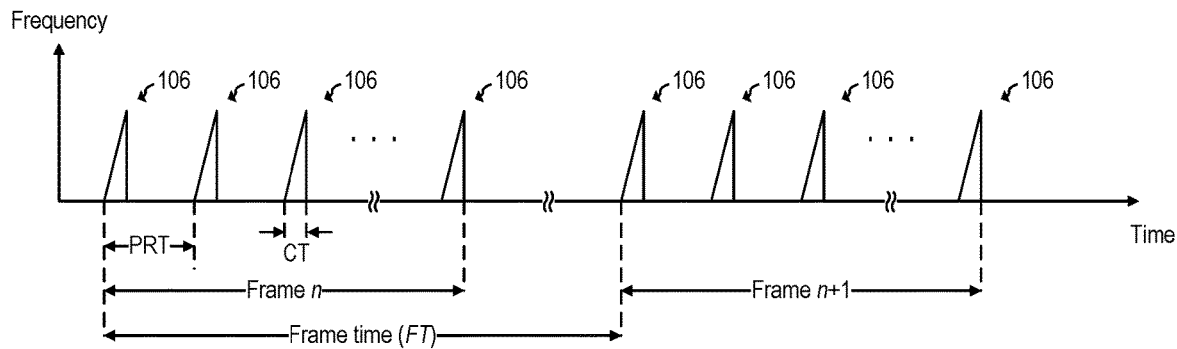
FIG. 2 illustrates a sequence of chirps transmitted by the TX antenna of FIG. 1, according to an embodiment of the present invention.

FIG. 2 illustrates a sequence of chirps 106 transmitted by TX antenna 114, according to an embodiment of the present invention. As shown by FIG. 2, chirps 106 are organized in a plurality of frames (also referred to as physical frames) and may be implemented as up-chirps. Some embodiments may use down-chirps or a combination of up-chirps and down-chirps, such as up-down chirps and down-up chirps. Other waveform shapes may also be used.

As shown in FIG. 2, each frame may include a plurality of chirps 106 (also referred to, generally, as pulses). For example, in some embodiments, the number of chirps in a frame is 64. Some embodiments may include more than 64 chirps per frame, such as 96 chirps, 128 chirps, 256 chirps, or more, or less than 64 chirps per frame, such as 32 chirps, 16 chirps, or less.

In some embodiments, frames are repeated every FT time. In some embodiments, FT time is 50 ms. A different FT time may also be used, such as more than 50 ms, such as 60 ms, 100 ms, 200 ms, or more, or less than 50 ms, such as 45 ms, 40 ms, or less.

In some embodiments, the FT time is selected such that the time between the beginning of the last chirp of frame n and the beginning of the first chirp of frame n+1 is equal to PRT. Other embodiments may use or result in a different timing.

The time between chirps of a frame is generally referred to as pulse repetition time (PRT). In some embodiments, the PRT is 5 ms. A different PRT may also be used, such as less than 5 ms, such as 4 ms, 2 ms, 0.5 ms, or less, or more than 5 ms, such as 6 ms, or more.

The duration of the chirp (from start to finish) is generally referred to as chirp time (CT). In some embodiments, the chirp time may be, e.g., 64 μs. Higher chirp times, such as 128 μs, or higher, may also be used. Lower chirp times, may also be used.

In some embodiments, the chirp bandwidth may be, e.g., 4 GHz. Higher bandwidth, such as 6 GHz or higher, or lower bandwidth, such as 2 GHz, 1 GHz, or lower, may also be possible.

In some embodiments, the sampling frequency of millimeter-wave radar sensor 102 may be, e.g., 1 MHz. Higher sampling frequencies, such as 2 MHz or higher, or lower sampling frequencies, such as 500 kHz or lower, may also be possible.

In some embodiments, the number of samples used to generate each chirp may be, e.g., 64 samples. A higher number of samples, such as 128 samples, or higher, or a lower number of samples, such as 32 samples or lower, may also be used to generate each chirp.

Figure 3:
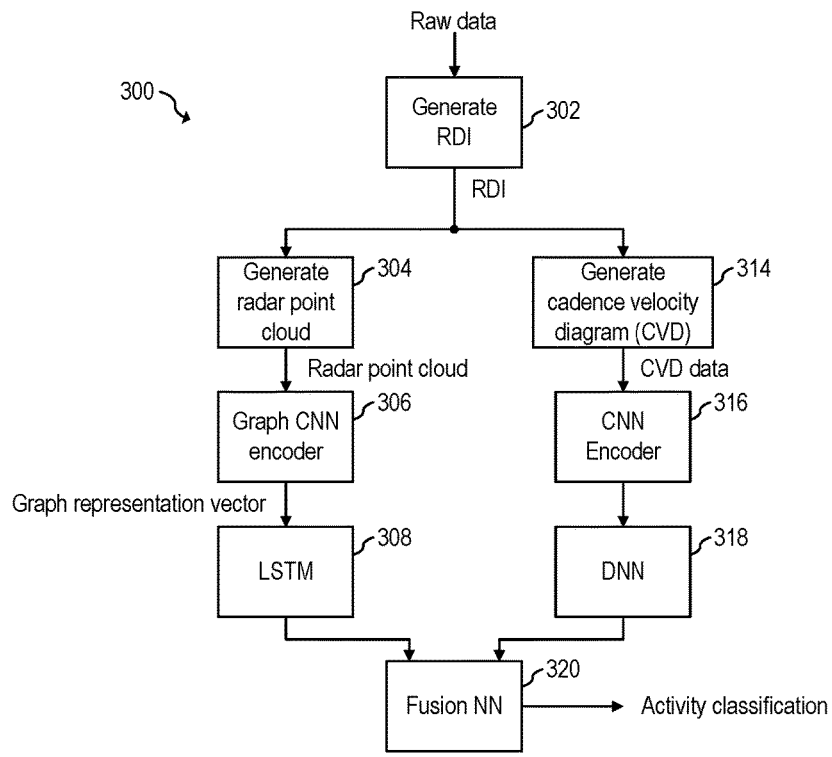
FIG. 3 shows an embodiment method for activity classification of a target, according to an embodiment of the present invention.

FIG. 3 shows embodiment method 300 for activity classification of a target, according to an embodiment of the present invention. Method 300 may be implemented by processing system 104.

Method 300 includes steps 302, 304, 306, 308, 314, 316, 318, and 320. In some embodiments, the sequence of steps including steps 304, 306, and 308 may be performed in parallel with the sequence of steps including steps 314, 316, and 318.

In some embodiments, steps 302, 304, 306, 308, 314, 316, 318, and 320 may be performed continuously as new raw data is received (e.g., in a windowing operation).

During step 302, a range-Doppler image (RDI) is generated based on raw data (e.g., $X_{out\_dig}(n)$) received from, e.g., millimeter-wave radar sensor 102. In some embodiments, the RDI may be generated in a conventional manner.

During step 304, a radar point cloud is generated. A radar point cloud may be understood as a scattered collection of points that represent one or more targets in a scene. In some embodiments, the radar point cloud includes, for each point of the radar point cloud, three-dimensional (3D) coordinates (e.g., Cartesian or Polar), an intensity value, and Doppler value.

During step 306, a graph encoder, such as a graph convolutional neural network (CNN) encoder, is used to generate a graph representation vector based on the radar point cloud (e.g., a graph representation of the radar point cloud) generated during step 304. In some embodiments, the graph representation vector includes additional edge information (e.g., edge weight) connecting each of the nodes (points of the radar point cloud) to each other. Such edge information may advantageously allow for extracting relationship values between points of the radar point cloud that may not be spatially adjacent (e.g., extracting a relationship value between points with 3D coordinates that are relatively far away, such as a point representing a hand and a point representing a foot). In some embodiments, such relationship values may advantageously aid in differentiating activities that may be similar. For example, even though the motion of a person falling and a person bending over to pick something may be similar, a person falling may exhibit uncontrolled limb motions while a person bending over may exhibit controlled limb motion. Such difference in limb motions may be used to distinguish between otherwise similar activities.

In some embodiments, steps 302, 302, and 306 are performed once per frame of raw data.

During step 308, a (e.g., bidirectional) long short-term memory (LSTM) neural network is used (e.g., after training) to (e.g., generate feature vectors and) classify the (e.g., sequential in time) the graph representation vectors generated during step 306. In some embodiments, temporal information is extracted from the graph representation vectors by using graph representation vectors that correspond to radar point clouds that are sequential in time. For example, in some embodiments, a plurality of RDIs that are sequential in time are generated during step 302, which cause the generation of a corresponding plurality of radar point clouds that are sequential in time (during step 308), which cause the graph representation vectors generated during step 306 to be sequential in time. Such graph representation vectors may be provided to the LSTM during step 308. The LSTM used during step 308 may be implemented in a conventional manner.

As a non-limiting example, in some embodiments, N radar point clouds that are sequential in time are generated during step 304 based on N sequential in time RDIs generated during step 302 (which are generated based on N sequential frames of raw data, where each frame of raw data is associated with a respective time step). A corresponding N graph representation vectors are generated during step 306 based on the N radar point clouds.

In some embodiments, N may be equal to 10. N having values higher than 10, such as 12, 16, or more, or N having values lower than 10, such as 8 or lower, may also be used.

During step 314, a cadence velocity diagram (CVD) is generated based on the RDI generated during step 302. A CVD may be understood as a diagram that expresses how the curves in the time-frequency-domain repeat. For example, in some embodiments, for N sequential RDIs generated during step 302, a Doppler bin is selected (e.g., such as the Doppler bin exhibiting highest intensity), the selected Doppler bins are stacked together, and an FFT is performed on the stacked Doppler bins to generated the CVD. In some embodiments, the resulting CVD captures the periodicity of movement of different body parts during the N time steps.

During step 316, a CNN encoder is used to generate a feature map based on the CVD. Such feature map is used during step 318 by a neural network, such as a deep neural network (DNN) to generate a feature vector.

In some embodiments, the CNN encoder used during step 316 may be implemented in a conventional manner. In some embodiments, the DNN used during step 318 may be implemented in a conventional manner.

In some embodiments, the neural network used during step 318 may include one or more fully-connected layers and/or a 1D CNN.

During step 320, a fusion neural network, which may include one or more fully-connected layers, is used to generate an activity classification based on the feature vectors generated during steps 308 and 318. In some embodiments, the output of the fusion neural network is a vector of size L, assigning a probability value to each of L activities, where L is a positive integer higher than 1. In some embodiments, the activity classification generated during step 320 may include just two activities (L=2), representing the activities of, e.g., a target falling or not falling. In some embodiments, the activity classification generated during step 320 may include more than two activities (L>2), representing more than two activities, such as walking, running, sitting, bending over, and falling. Other implementations are also possible.

In some embodiments, in a particular classification cycle (for a particular output of the fusion NN during step 320), the number of time steps N used for generating the CVD data during step 314 is the same and correspond to the time steps used during step 308 by the LSTM neural network.

Figure 4:
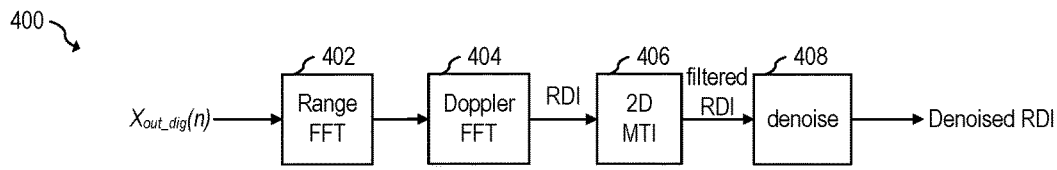
FIG. 4 shows a flow chart of an embodiment method for generating an RDI, according to an embodiment of the present invention.

FIG. 4 shows a flow chart of embodiment method 400 for generating an RDI, according to an embodiment of the present invention. Step 302 may be implemented as method 400.

During step 402, a range fast Fourier transform (FFT) is performed on the raw digital data $x_{out\_dig}(n)$ (e.g., on data from each receiving channel, e.g., from each receiving antenna 116). For example, in some embodiments, a windowed FFT having a length of a chirp (e.g., 106) is calculated for each of a predetermined number of chirps (e.g., all chirps) in a frame. The result of the range FFT is an indication of energy distribution across ranges for each chirp.

During step 404, a Doppler FFT is performed on the range FFT data (e.g., for each receiving antenna 116) generated during step 402. For example, in some embodiments, an FFT is calculated across each range bin over a number of consecutive periods to extract Doppler information. The result of step 404 are range Doppler maps (also known are range-Doppler images or RDIs) for each of the receiving channels (e.g., for each receiving antenna 116).

During step 406, two-dimensional (2D) moving target indication (MTI) filtering is applied to each RDI to generate first filtered images. In some embodiments, performing MTI filtering serves to discriminate a target against the clutter. For example, in some embodiments, after MTI filtering is performed on the RDIs, only targets with high motion are retained as their energy varies across Doppler images. Thus, in some embodiments, after 2D MTI filtering, a target may be identifiable in the filtered RDIs while information about the background may be partially or fully removed from the filtered RDIs. In some embodiments, the 2D MTI filter is implemented as a first order finite impulse response (FIR) filter.

In some embodiments, only single person scenarios are considered. Thus, in some embodiments, outlier points (points far from the cluster of points) are removed as noise during step 408.

In some embodiments, method 400 is performed for each frame of raw data $x_{out\_dig}(n)$, thereby generating an RDI per frame of raw data $x_{out\_dig}(n)$.

Figure 5:
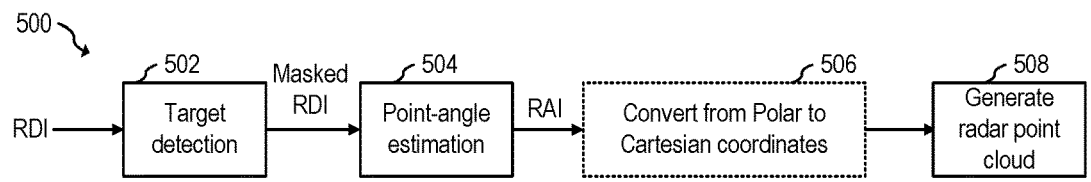
FIG. 5 shows a flow chart of an embodiment method for generating a radar point cloud, according to an embodiment of the present invention.

FIG. 5 shows a flow chart of embodiment method 500 for generating a radar point cloud, according to an embodiment of the present invention. Step 304 may be implemented as method 500.

During step 502, target detection is performed on an RDI (e.g., received from step 302). In some embodiments, target detection is performed using constant false alarm rate (CFAR), such as ordered-statistic (OS) CFAR (OS-CFAR).

In some embodiments, target detection is performed by comparing each point of the RDI with a predetermined threshold, and selecting the points above the threshold, along with points (e.g., directly adjacent) to the points above the threshold. In some embodiments, the selection of points includes points in a 5×3 window around each point above the threshold. Other selection mechanisms may also be used.

The output of step 502 is a masked RDI that includes the selected points and is zero for unselected points.

During step 504, point-angle estimation is performed in a conventional manner for each of the selected points in the masked RDI generated during step 502. For example, in some embodiments, 2D digital (e.g., Barlett) beamforming (e.g., 2-D Capon) is applied to transform the data across virtual channels from rectangular array configuration into 2-D range-angle image (RAI).

During step 506, a conversion from Polar coordinates to Cartesian coordinates is performed. As will be described in more detail below, the use of Cartesian coordinates may be advantageous for the training of the graph CNN encoder used during step 306. In some embodiments, step 506 is omitted.

In some embodiments, the conversion from Polar coordinates to Cartesian coordinates may be performed by using Equation 1:

$$\begin{bmatrix} x \\ y \\ z \end{bmatrix} = \begin{bmatrix} 1 & 0 & 0 \\ 0 & \cos(\theta_{tilt}) & \sin(\theta_{tilt}) \\ 0 & -\sin(\theta_{tilt}) & \cos(\theta_{tilt}) \end{bmatrix} \begin{bmatrix} r \cdot \cos(\theta_{ele}) \cdot \sin(\theta_{azi}) \\ r \cdot \cos(\theta_{ele}) \cdot \sin(\theta_{azi}) \\ r \cdot \sin(\theta_{ele}) \end{bmatrix} + \begin{bmatrix} 0 \\ 0 \\ h \end{bmatrix} \quad (1)$$

where (x,y,z) represent the 3D Cartesian coordinates of the radar point, $(r,\theta_{ele},\theta_{azi})$ represent the 3D Polar coordinates of the radar point, $\theta_{tilt}$ represents the tilt angle of the center of the field-of-view of millimeter-wave radar sensor 102 with respect to the floor, and h represents the height location of the millimeter-wave radar sensor 102 with respect to the floor.

During step 508, a set of detection points is generated, which together form the radar point cloud. In some embodiments, each detection point includes: 3D coordinates, a signal strength value (indicative of the signal strength of the target located at the 3D coordinates), and a Doppler value (indicative of the level of movement of the target at the 3D coordinates). In some embodiments, the 3D coordinates are Cartesian coordinates (e.g., x, y, z) (e.g., if step 506 is performed). In some embodiments, the 3D coordinates are Polar coordinates (e.g., range, azimuth angle, and elevation angle) (e.g., if step 506 is not performed).

In some embodiments, the radar point cloud is represented as a matrix having each of the radar points as columns and each of the (e.g., 5) attributes (e.g., x, y, z, intensity, and Doppler) as rows in a concatenated manner.

Figure 6A:
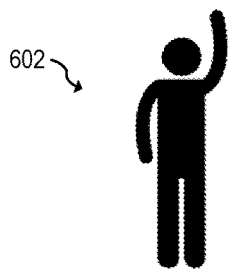
FIGS. 6A and 6B illustrate, respectively, a target, and a representation of a radar point cloud associated with the target and generated using the method of FIG. 5, according to an embodiment of the present invention.
Figure 6B:
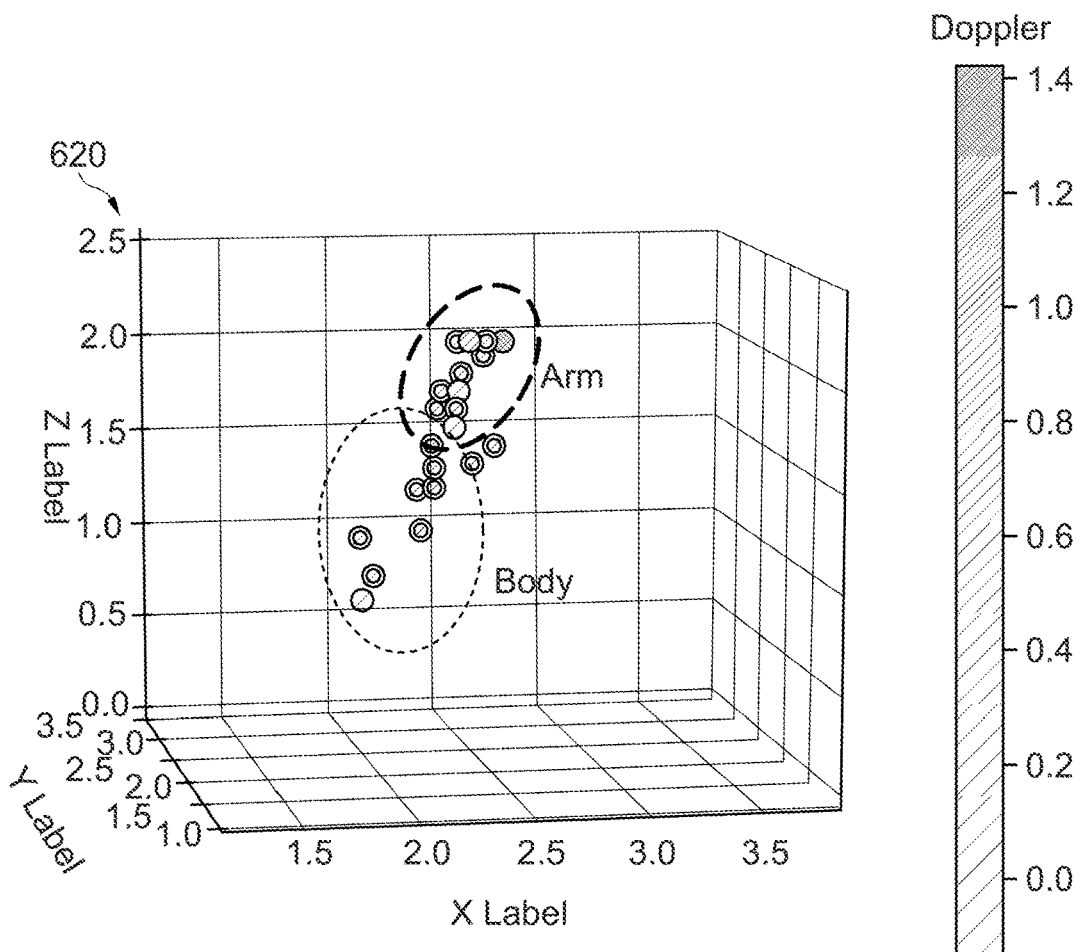

FIGS. 6A and 6B illustrate, respectively, target 602, and a representation of radar point cloud 620 associated with target 602 and generated using method 500 (including step 506), according to an embodiment of the present invention.

As shown in FIG. 6A, a human target 602 is standing and lifting his arm. As shown in FIG. 6B, different portions of human target 602 are captured with radar points. Each radar point has a respective Doppler velocity, which is based on the movement of the particular body part at the time step associated with the radar point cloud 620.

As illustrated in FIG. 6B, the body of human target 602 is relatedly still (low Doppler velocity) while the arm exhibits a high Doppler velocity (which is related to the movement associated with the lifting of the arm).

Figure 7:
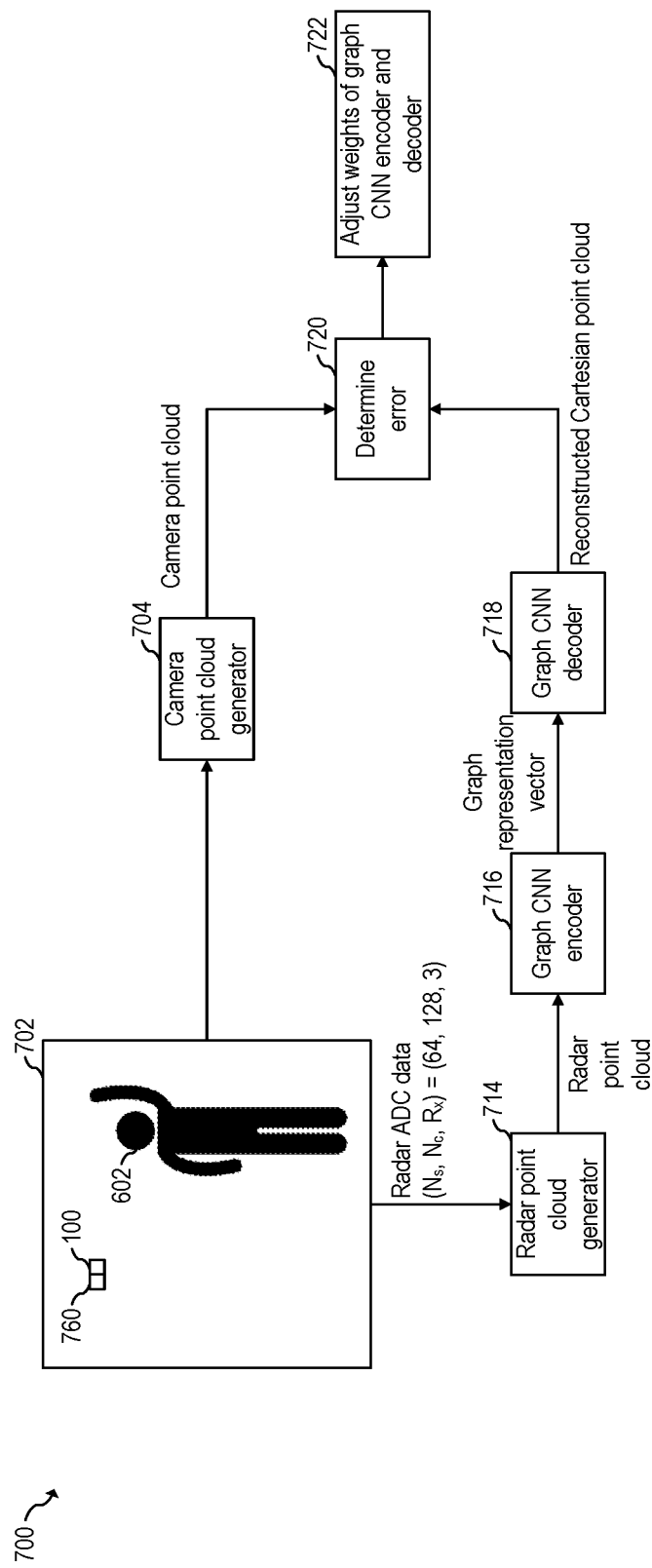
FIG. 7 shows a block diagram illustrating a method for training a graph CNN encoder 716, according to an embodiment of the present invention.
Figure 8:
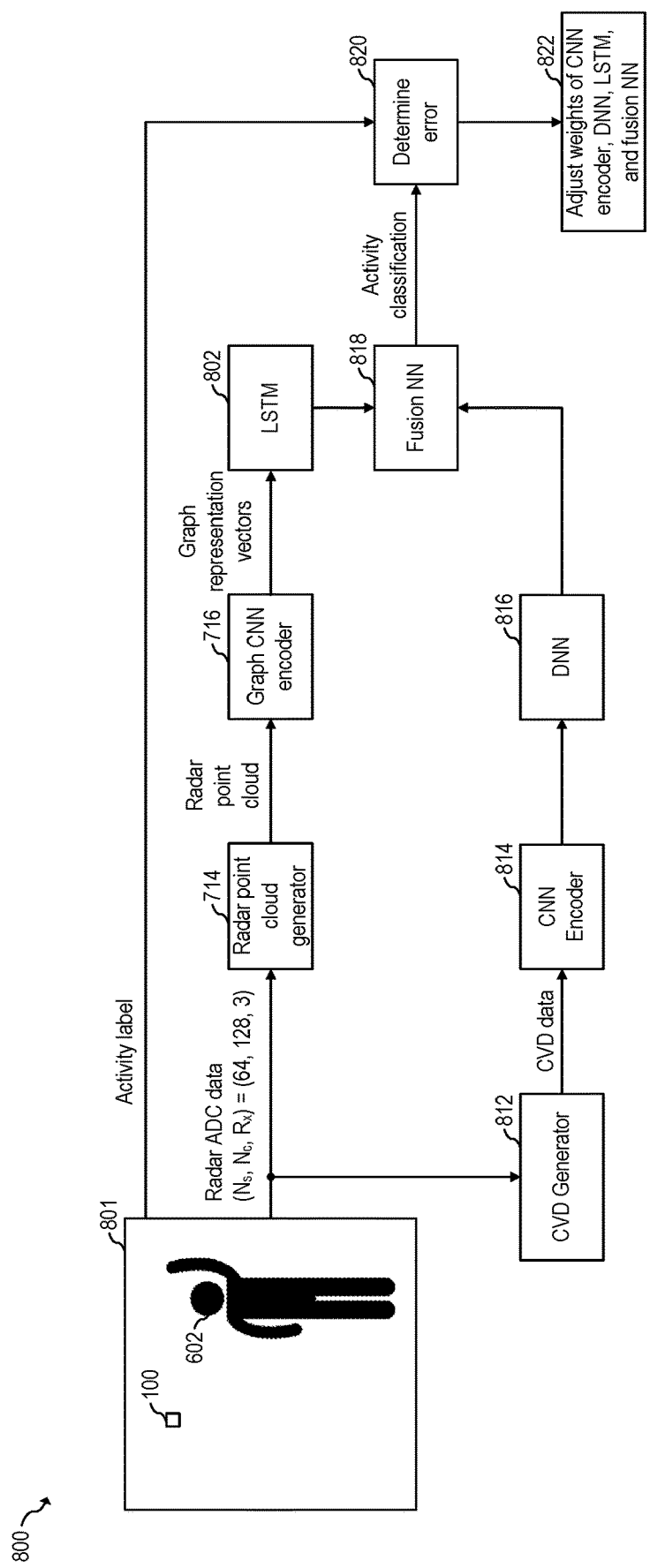
FIG. 8 illustrates a block diagram illustrating a method for training various neural networks used during the method of FIG. 3, according to an embodiment of the present invention.

In some embodiments, the neural networks used during method 300 may be trained in a supervised manner, e.g., using a two-step process. In a first step, the graph CNN encoder used during step 306 is trained first (e.g., using information from a camera as the ground truth). Once the graph CNN encoder is trained, the neural networks used during steps 308, 316, 318, and 320 are trained in a supervised manner. FIGS. 7 and 8 illustrate the first and second training steps, respectively.

FIG. 7 illustrates block diagram 700 illustrating a method for training graph CNN encoder 716 (e.g., used during step 306), according to an embodiment of the present invention.

Block 702 illustrates a scene (e.g., a room) equipped with millimeter-wave radar system 100, a camera system 760, and a human performing various activities (e.g., raising a hand, walking, sitting, falling, etc.). Camera system 760 and millimeter-wave radar system 100 simultaneously capture the same activity of target 602.

Camera point cloud generator 704 generates a camera point cloud based on an image capture by camera system 760. The camera point cloud may be generated in a conventional manner, such as by using the Detectron2 platform from Facebook.

As illustrated in FIG. 7, in some embodiments, the number of chirps in a frame $N_c$ is 128, the number transmit samples per chirp $N_s$ is 64, and the number of receiving antennas 116 $R_x$ is 3.

Radar point cloud generator 714 generates a radar point cloud based on the radar signals captured by millimeter-wave radar system 102 (e.g., at the same time as the image captured by camera system 760). In some embodiments, radar point generator 714 may generate the radar point cloud by performing steps 302 and 304.

In some embodiments, the radar point cloud generated by radar point cloud generator 714 includes, for each point, Cartesian coordinates, which advantageously are easier to compare with the camera point cloud generated by camera point cloud generator 704.

Graph CNN encoder 716 generates a graph representation vector based on the radar point cloud (e.g., by performing step 306).

Graph CNN decoder 718 generates a reconstructed Cartesian point cloud based on the graph representation vector generated by graph CNN encoder 716.

Blocks 720 and 722 illustrate the adjustment of the weights of graph CNN encoder 716 and graph CNN decoder 718 so that the reconstructed Cartesian point cloud approximates the camera point cloud (which is treated as the ground truth).

In some embodiments, the training illustrated by block diagram 700 may be performed frame by frame and, thus, may not include any temporal information.

FIG. 8 illustrates block diagram Boo illustrating a method for training CNN encoder 814, DNN 816, LSTM 802, and fusion neural network 818 (e.g., used during steps 316, 318, 308, and 320, respectively), according to an embodiment of the present invention.

The training illustrated by block diagram 800 assumes that graph CNN encoder 716 is already trained (e.g., using method 700).

In some embodiments, the training illustrated by block diagram 800 is performed per activity. For example, for a particular activity, an activity label and a plurality of frames are produced by block 801. Once fusion neural network 818 produces a prediction of the activity classification, such prediction is compared with the activity label and the weights of the neural networks in blocks 802, 814, 816, and 818 are adjusted to reduced such error (as illustrated by blocks 820 and 822).

Block 801 illustrates a scene (e.g., a room) equipped with millimeter-wave radar system 100, and a human performing various activities (e.g., raising a hand, walking, sitting, falling, etc.).

In a similar manner as described with respect to FIG. 7, radar point cloud generator 714 generates a radar point cloud based on the radar signals captured by millimeter-wave radar system 102 (e.g., by performing steps 302 and 304) and graph CNN encoder 716 generates a graph representation vector based on the radar point cloud (e.g., by performing step 306).

Graph representation vectors corresponding to a plurality of frames associated with one activity is provided to (e.g., bidirectional) LSTM 802 (e.g., which is used during step 308).

CVD generator 812 generates CVD data (e.g., by performing 302 and 314) based on a plurality of frames associated with the one activity. In some embodiments, step 302 shared between radar point cloud generator 714 and CVD generator 812.

CNN encoder 814 receives the CVD data. DNN 816 receives data from an output of CNN encoder 814. Fusion NN 818 receives data from an output of LSTM 802 and an output of DNN 816 and generates an activity classification prediction based on the data received from LSTM 802 and DNN 816. Such prediction is compared with the activity label and the weights of the neural networks in blocks 802, 814, 816, and 818 are adjusted to reduced such error (as illustrated by blocks 820 and 822).

In some embodiments, blocks 714, 716, 802, 812, 814, 816, and 818 may be used (e.g., after training) during inference to perform method 300 and produce an activity classification based on the raw data received from millimeter-wave radar sensor 102. Blocks 714, 716, 802, 812, 814, 816, and 818 may be implemented by processing system 104.

FIGS. 9A and 9B illustrate a possible implementation of graph CNN encoder 716 and graph CNN decoder 718, according to an embodiment of the present invention.

As shown in FIG. 9A, a radar point cloud (e.g., generated by radar point cloud generator 714) is received by input transformation network 902. As shown, the dimensionality of the received radar point cloud is n (e.g., 64) times 5 (the 5 features: x, y, z, intensity, and Doppler).

Input transformation network 902 may be understood as a mini neural network that predicts affine transformation matrix which is applied to the input point clouds, making it invariant to geometric modifications.

The output of input transformation network 902 is fed to dynamic graph CNN autoencoder 904, which first encodes to produce a graph representation vectors, and then decodes to reconstruct a Cartesian point cloud based on the graph representation vector.

As shown in FIG. 9B, the EdgeConv block receives a tensor of shape n×f and computes edge features of each point in k-nearest neighbor (k-nn) graph by a multi-layer perceptron (mlp) with the number of layer units denoted as $\{a_1, a_2, \ldots, a_n\}$.

Additional details of the operation and structure of graph CNN encoder 716 and graph CNN decoder 718 illustrated in FIGS. 9A and 9B may be found in the paper entitled "Cross-modal Learning of Graph Representations using Radar Point Cloud for Long-Range Gesture Recognition," by Souvik Hazra, Hao Feng, Gamze Naz Kiprit, Michael Stephan, Lorenzo Servadei, Robert Wille, Robert Weigel, Avik Santra, and published in 2022 by asXiv as 2203.17066, which is incorporated herein by reference.

Figure 10:
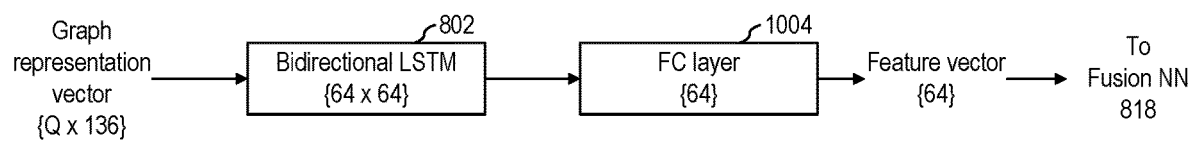
FIG. 10 illustrates a block diagram of a possible implementation of the path from the output of the graph CNN encoder of FIG. 7 to the input of the fusion neural network of FIG. 8, according to an embodiment of the present invention.

FIG. 10 illustrates block diagram moo of a possible implementation of the path from the output of graph CNN encoder 716 to the input of fusion neural network 818, according to an embodiment of the present invention.

As shown in FIG. 10, in some embodiments, the graph representation vectors generated by graph CNN encoder 716 include 136 dimensions per vector. Q vectors (corresponding to Q frames of raw data) are stacked to create a Q×136 tensor, which is fed to, e.g., two 64-units bidirectional LSTM layers 802. Fully-connected layer 1004 produce a (e.g., 64 dimension) feature vector for activity classification.

Advantages of some embodiments include the capability of producing accurate activity classification (with, e.g., negligible false positives) at short distances (e.g., less than 1 m) as well as longer distances (e.g., between 1 m and 30 m), which is advantageously superior than some conventional methods that rely on spectrogram, which may have degraded performance beyond 1 m.

Example embodiments of the present invention are summarized here. Other embodiments can also be understood from the entirety of the specification and the claims filed herein.

Example 1. A method including: receiving raw data from a millimeter-wave radar sensor; generating a first radar-Doppler image based on the raw data; generating a first radar point cloud based on the first radar-Doppler image; using a graph encoder to generate a first graph representation vector indicative of one or more relationships between two or more parts of the target based on the first radar point cloud; generating a first cadence velocity diagram indicative of a periodicity of movement of one or more parts of the target based on the first radar-Doppler image; and classifying an activity of a target based on the first graph representation vector and the first cadence velocity diagram.

Example 2. The method of example 1, further including: generating a plurality of graph representation vectors that corresponds to frames of the raw data that are sequential in time, the plurality of graph representation vectors including the first graph representation vector; and providing the plurality of graph representation vectors to a long short-term memory (LSTM) neural network, where classifying the activity of the target is based on an output of the LSTM neural network.

Example 3. The method of one of examples 1 or 2, further including providing the first cadence velocity diagram to a convolutional neural network (CNN) encoder, where classifying the activity of the target is based on the CNN encoder.

Example 4. The method of one of examples 1 to 3, further including: providing an output of the CNN encoder to a deep neural network (DNN); providing an output of the DNN to a fusion neural network; and providing the output of the LSTM neural network to the fusion neural network, where classifying the activity of the target is based on an output of the fusion neural network.

Example 5. The method of one of examples 1 to 4, where the fusion neural network includes a fully-connected layer.

Example 6. The method of one of examples 1 to 5, further including training the graph encoder before training the LSTM neural network, the CNN encoder, the DNN, and the fusion neural network.

Example 7. The method of one of examples 1 to 6, where training the graph encoder includes: generating a first training camera point cloud based on an output of a camera, where the camera has a field of view directed towards a scene, where the millimeter-wave radar sensor has a field of view directed towards the scene; generating a first training radar point cloud based on an output of the millimeter-wave radar sensor, where the first training radar point cloud corresponds to the first training camera point cloud; using the graph encoder to generate a first training graph representation vector based on the first training radar point cloud; using a graph decoder to generate a second training point cloud based on the first training graph representation vector; comparing the first training camera point cloud with the second training point cloud to generate error data; and adjusting one or more weights of the graph encoder based on the error data.

Example 8. The method of one of examples 1 to 7, where the first radar point cloud includes, for each point of the first radar point cloud, three-dimensional coordinates, an intensity value, and a Doppler value.

Example 9. The method of one of examples 1 to 8, further including generating a first point-angle image based on the first radar-Doppler image, where generating the first radar point cloud includes generating the first radar point cloud based on the first point-angle image.

Example 10. The method of one of examples 1 to 9, further including generating a masked first radar-Doppler image from the first radar-Doppler image based on an intensity of each point of the first radar-Doppler image, where generating the first point-angle image includes generating the first point-angle image based on the masked first radar-Doppler image.

Example 11. The method of one of examples 1 to 10, where generating the masked first radar-Doppler image includes using a constant false alarm rate (CFAR) detector.

Example 12. The method of one of examples 1 to 11, where generating the masked first radar-Doppler image includes: selecting points of the first radar-Doppler image having an intensity higher than a predetermined threshold; and for each selected point, identifying one or more neighboring points in the first radar-Doppler image, where the masked first radar-Doppler image includes the selected points and the identified neighboring points, and where non-selected points and points not identified as neighboring points are not included in the masked first radar-Doppler image.

Example 13. The method of one of examples 1 to 12, where generating the first point-angle image includes performing Barlett beamforming to transform the first radar-Doppler image to a range-angle image.

Example 14. The method of one of examples 1 to 13, further including: transmitting radar signals towards a scene including the target; receiving reflected radar signals from the scene; and generating the first radar-Doppler image based on the reflected radar signals.

Example 15. The method of one of examples 1 to 14, where the target is a person, where the first graph representation vector is indicative of one or more relationships between two or more body parts of the person, where the first cadence velocity diagram is indicative of a periodicity of movement of one or more body parts of the person, and where classifying the activity of the target includes determining whether the person is falling or not falling.

Example 16. The method of one of examples 1 to 15, where the graph encoder is a graph convolutional neural network (CNN) encoder.

Example 17. A radar system including: a radar sensor configured to transmit a plurality of radar signals towards a scene, receive a plurality of reflected radar signals from the scene, and generate raw data based on the plurality of reflected radar signals; and a processing system configured to: generate a first radar image based on the raw data, generate a first radar point cloud based on the first radar image, use a graph encoder to generate a first graph representation vector indicative of one or more relationships between two or more parts of the target based on the first radar point cloud, generate a first cadence velocity diagram indicative of a periodicity of movement of one or more parts of the target based on the first radar image, and classify an activity of a target located in the scene based on the first graph representation vector and the first cadence velocity diagram.

Example 18. The radar system of example 17, where the processing system is further configured to: generate a plurality of graph representation vectors that corresponds to frames of the raw data that are sequential in time, the plurality of graph representation vectors including the first graph representation vector; and provide the plurality of graph representation vectors to a recurrent neural network, where the processing system is configured classify the activity of the target based on an output of the recurrent neural network.

Example 19. The radar system of one of examples 17 or 18, where the recurrent neural network includes a bi-directional long short-term memory (LSTM) neural network.

Example 20. A radar system including: a millimeter-wave radar sensor configured to transmit a plurality of radar signals towards a scene, receive a plurality of reflected radar signals from the scene, and generate raw data based on the plurality of reflected radar signals; and a processing system configured to: generate a plurality of radar-Doppler images based on the raw data, generate a plurality of radar point clouds based on the plurality of radar-Doppler images, use a graph encoder to generate a plurality of graph representation vectors indicative of one or more relationships between two or more parts of the target based on the plurality of radar point clouds, generate a first cadence velocity diagram indicative of a periodicity of movement of one or more parts of the target based on the plurality of radar-Doppler images, and classify an activity of a target located in the scene based on the plurality of graph representation vectors and the first cadence velocity diagram.

While this invention has been described with reference to illustrative embodiments, this description is not intended to be construed in a limiting sense. Various modifications and combinations of the illustrative embodiments, as well as other embodiments of the invention, will be apparent to persons skilled in the art upon reference to the description. It is therefore intended that the appended claims encompass any such modifications or embodiments.

What is claimed is:

1. A method comprising:
   receiving raw data from a millimeter-wave radar sensor;
   generating a first radar-Doppler image based on the raw data;
   generating a first radar point cloud based on the first radar-Doppler image;
   using a graph encoder to generate a first graph representation vector indicative of one or more relationships between two or more parts of a target based on the first radar point cloud;
   generating a first cadence velocity diagram indicative of a periodicity of movement of one or more parts of the target based on the first radar-Doppler image; and
   classifying an activity of the target based on the first graph representation vector and the first cadence velocity diagram.

2. The method of claim 1, further comprising:
   generating a plurality of graph representation vectors that corresponds to frames of the raw data that are sequential in time, the plurality of graph representation vectors comprising the first graph representation vector; and providing the plurality of graph representation vectors to a long short-term memory (LSTM) neural network, wherein classifying the activity of the target is based on an output of the LSTM neural network.

3. The method of claim 2, further comprising providing the first cadence velocity diagram to a convolutional neural network (CNN) encoder, wherein classifying the activity of the target is based on the CNN encoder.

4. The method of claim 3, further comprising:
providing an output of the CNN encoder to a deep neural network (DNN);
providing an output of the DNN to a fusion neural network; and
providing the output of the LSTM neural network to the fusion neural network, wherein classifying the activity of the target is based on an output of the fusion neural network.

5. The method of claim 4, wherein the fusion neural network comprises a fully-connected layer.

6. The method of claim 4, further comprising training the graph encoder before training the LSTM neural network, the CNN encoder, the DNN, and the fusion neural network.

7. The method of claim 6, wherein training the graph encoder comprises:
generating a first training camera point cloud based on an output of a camera, wherein the camera has a field of view directed towards a scene, wherein the millimeter-wave radar sensor has a field of view directed towards the scene;
generating a first training radar point cloud based on an output of the millimeter-wave radar sensor, wherein the first training radar point cloud corresponds to the first training camera point cloud;
using the graph encoder to generate a first training graph representation vector based on the first training radar point cloud;
using a graph decoder to generate a second training point cloud based on the first training graph representation vector;
comparing the first training camera point cloud with the second training point cloud to generate error data; and
adjusting one or more weights of the graph encoder based on the error data.

8. The method of claim 1, wherein the first radar point cloud comprises, for each point of the first radar point cloud, three-dimensional coordinates, an intensity value, and a Doppler value.

9. The method of claim 1, further comprising generating a first point-angle image based on the first radar-Doppler image, wherein generating the first radar point cloud comprises generating the first radar point cloud based on the first point-angle image.

10. The method of claim 9, further comprising generating a masked first radar-Doppler image from the first radar-Doppler image based on an intensity of each point of the first radar-Doppler image, wherein generating the first point-angle image comprises generating the first point-angle image based on the masked first radar-Doppler image.

11. The method of claim 10, wherein generating the masked first radar-Doppler image comprises using a constant false alarm rate (CFAR) detector.

12. The method of claim 10, wherein generating the masked first radar-Doppler image comprises:
selecting points of the first radar-Doppler image having an intensity higher than a predetermined threshold; and
for each selected point, identifying one or more neighboring points in the first radar-Doppler image, wherein the masked first radar-Doppler image comprises the selected points and the identified neighboring points, and wherein non-selected points and points not identified as neighboring points are not comprised in the masked first radar-Doppler image.

13. The method of claim 9, wherein generating the first point-angle image comprises performing Barlett beamforming to transform the first radar-Doppler image to a range-angle image.

14. The method of claim 1, further comprising:
transmitting radar signals towards a scene comprising the target;
receiving reflected radar signals from the scene; and
generating the first radar-Doppler image based on the reflected radar signals.

15. The method of claim 1, wherein the target is a person, wherein the first graph representation vector is indicative of one or more relationships between two or more body parts of the person, wherein the first cadence velocity diagram is indicative of a periodicity of movement of one or more body parts of the person, and wherein classifying the activity of the target comprises determining whether the person is falling or not falling.

16. The method of claim 1, wherein the graph encoder is a graph convolutional neural network (CNN) encoder.

17. A radar system comprising:
a radar sensor configured to transmit a plurality of radar signals towards a scene, receive a plurality of reflected radar signals from the scene, and generate raw data based on the plurality of reflected radar signals; and
a processing system configured to:
generate a first radar image based on the raw data,
generate a first radar point cloud based on the first radar image,
use a graph encoder to generate a first graph representation vector indicative of one or more relationships between two or more parts of a target based on the first radar point cloud,
generate a first cadence velocity diagram indicative of a periodicity of movement of one or more parts of the target based on the first radar image, and
classify an activity of the target located in the scene based on the first graph representation vector and the first cadence velocity diagram.

18. The radar system of claim 17, wherein the processing system is further configured to:
generate a plurality of graph representation vectors that corresponds to frames of the raw data that are sequential in time, the plurality of graph representation vectors comprising the first graph representation vector; and
provide the plurality of graph representation vectors to a recurrent neural network, wherein the processing system is configured to classify the activity of the target based on an output of the recurrent neural network.

19. The radar system of claim 18, wherein the recurrent neural network comprises a bi-directional long short-term memory (LSTM) neural network.

20. A radar system comprising:
a millimeter-wave radar sensor configured to transmit a plurality of radar signals towards a scene, receive a plurality of reflected radar signals from the scene, and generate raw data based on the plurality of reflected radar signals; and
a processing system configured to:
generate a plurality of radar-Doppler images based on the raw data, generate a plurality of radar point clouds based on the plurality of radar-Doppler images,
use a graph encoder to generate a plurality of graph representation vectors indicative of one or more relationships between two or more parts of a target based on the plurality of radar point clouds,
generate a first cadence velocity diagram indicative of a periodicity of movement of one or more parts of the target based on the plurality of radar-Doppler images, and
classify an activity of the target located in the scene based on the plurality of graph representation vectors and the first cadence velocity diagram.

\* \* \* \* \*